(12) United States Patent
O'Connell

(10) Patent No.: US 9,039,670 B2
(45) Date of Patent: May 26, 2015

(54) REFASTENABLE TRAINING PANT WITH OFFSET AND THIN SEAM

(75) Inventor: Susan O'Connell, Chesterbrook, PA (US)

(73) Assignee: FIRST QUALITY BABY PRODUCTS, LLC, Great Neck, NY (US)

( * ) Notice: Subject to any disclaimer, the term of this patent is extended or adjusted under 35 U.S.C. 154(b) by 0 days.

(21) Appl. No.: 13/412,470

(22) Filed: Mar. 5, 2012

(65) Prior Publication Data

US 2013/0231627 A1 Sep. 5, 2013

(51) Int. Cl.
| | | |
|---|---|---|
| A61F 13/20 | (2006.01) | |
| A61F 13/62 | (2006.01) | |
| A61F 13/493 | (2006.01) | |
| A61F 13/496 | (2006.01) | |

(52) U.S. Cl.
CPC ............ *A61F 13/622* (2013.01); *A61F 13/493* (2013.01); *A61F 13/4963* (2013.01)

(58) Field of Classification Search
CPC ... A61F 13/62; A61F 13/5622; A61F 13/565; A61F 13/4963
USPC ............. 604/385.24, 391, 392, 394, 386, 396
See application file for complete search history.

(56) References Cited

U.S. PATENT DOCUMENTS

| | | | |
|---|---|---|---|
| 4,854,989 A | 8/1989 | Singheimer | |
| 6,447,497 B1 * | 9/2002 | Olson | ............................ 604/389 |
| 6,893,426 B1 | 5/2005 | Popp et al. | |
| 6,994,761 B2 | 2/2006 | Klemp et al. | |
| 7,805,818 B2 * | 10/2010 | Horn et al. | ........................ 24/448 |
| 2002/0042600 A1 | 4/2002 | Datta et al. | |
| 2003/0055389 A1 * | 3/2003 | Sanders et al. | ................ 604/358 |
| 2007/0049890 A1 | 3/2007 | Popp et al. | |
| 2010/0030176 A1 | 2/2010 | Beckert et al. | |
| 2010/0130956 A1 | 5/2010 | Wennerback | |
| 2010/0191213 A1 | 7/2010 | O'Connell | |
| 2010/0228211 A1 | 9/2010 | Becker et al. | |
| 2010/0268183 A1 | 10/2010 | Een et al. | |
| 2011/0319846 A1 | 12/2011 | Rinnert et al. | |

FOREIGN PATENT DOCUMENTS

WO WO 2006062810 A1 * 6/2006

OTHER PUBLICATIONS

International Search Report of PCT/US13/29122 dated Jun. 27, 2013.
Written Opinion of the International Searching Authority for PCT/US13/29122 dated Jun. 27, 2013.
Invitation to Pay Additional Fees and Where Applicable Protest Fee of PCT/US13/29122 dated Apr. 26, 2013.

* cited by examiner

*Primary Examiner* — Melanie Hand
*Assistant Examiner* — Aundria Hairell
(74) *Attorney, Agent, or Firm* — Amster, Rothstein & Ebenstein LLP

(57) ABSTRACT

An absorbent article including a chassis having a front waist portion and a back waist portion, front side panels having an inside surface and an outside surface, back side panels having an inside surface and an outside surface, and seams adapted to attach the front side panels to the back side panels in an overlapped configuration offset toward the front waist portion, the seams made up of one or more fastening components attached to the outside surface of each of the back side panels.

46 Claims, 5 Drawing Sheets

US 9,039,670 B2

REFASTENABLE TRAINING PANT WITH OFFSET AND THIN SEAM

FIELD

The present invention relates generally to disposable absorbent articles such as training pants, and more specifically to refastenable training pants with an offset and thin seam.

BACKGROUND

Infants and other incontinent individuals may wear disposable absorbent articles to absorb and contain fluids and exudates discharged from the body. Absorbent articles function to contain the discharged materials in isolation from the body of the wearer on one side, and from the wearers garments and/or bedding on the other. Absorbent articles are typically constructed from a combination of liquid and vapor pervious and impervious materials which respectively allow the passage of liquid into the absorbent article and prevent its exit therefrom.

One type of absorbent article, known as a "training pant," is permanently or releasably seamed together to provide a pant-like product, which can be useful when "potty training" a child. In the case of releasable seams, the training pant may function so as to be applied either as a diaper or a pant. This is particularly useful for active children who are still in the training stages, since the releasable seams allow the product to be easily checked without having to pull the product downwards.

SUMMARY OF THE INVENTION

According to an exemplary embodiment of the invention, an absorbent article may include a chassis comprising a front waist portion and a back waist portion; one or more front side panels extending outwardly from the front waist portion, each of the one or more front side panels having an inside surface, an outside surface, a proximal edge, and a distal edge; one or more back side panels extending outwardly from the back waist portion, each of the one or more back side panels having an inside surface, an outside surface, a proximal edge, and a distal edge; one or more fastening components attached to at least one of the outside surface of each of the one or more back side panels and the inside surface of each of the one or more front side panels; and one or more seams comprising at least one of the one or more front side panels, at least one of the one or more back side panels, and at least one of the one or more fastening components, the one or more seams being adapted to attach the one or more front side panels to the one or more back side panels in an overlapped configuration offset toward the front waist portion.

According to an alternative example embodiment of the invention, an absorbent article may include a chassis comprising a front waist portion and a back waist portion; one or more front side panels extending outwardly from the front waist portion, each of the one or more front side panels having an inside surface, an outside surface, a proximal edge, and a distal edge; one or more back side panels extending outwardly from the back waist portion, each of the one or more back side panels having an inside surface, an outside surface, a proximal edge, and a distal edge; one or more sealed seams comprising at least a portion of one of the one or more front side panels and at least a portion of one of the one or more back side panels, the one or more seams being adapted to attach the one or more front side panels to the one or more back side panels in an overlapped configuration offset toward the front waist portion.

Other features and advantages of embodiments of the invention will become readily apparent from the following detailed description, the accompanying drawings and the appended claims.

BRIEF DESCRIPTION OF THE DRAWINGS

The features and advantages of exemplary embodiments of the present invention will be more fully understood with reference to the following, detailed description when taken in conjunction with the accompanying figures, wherein.

Figure 1:
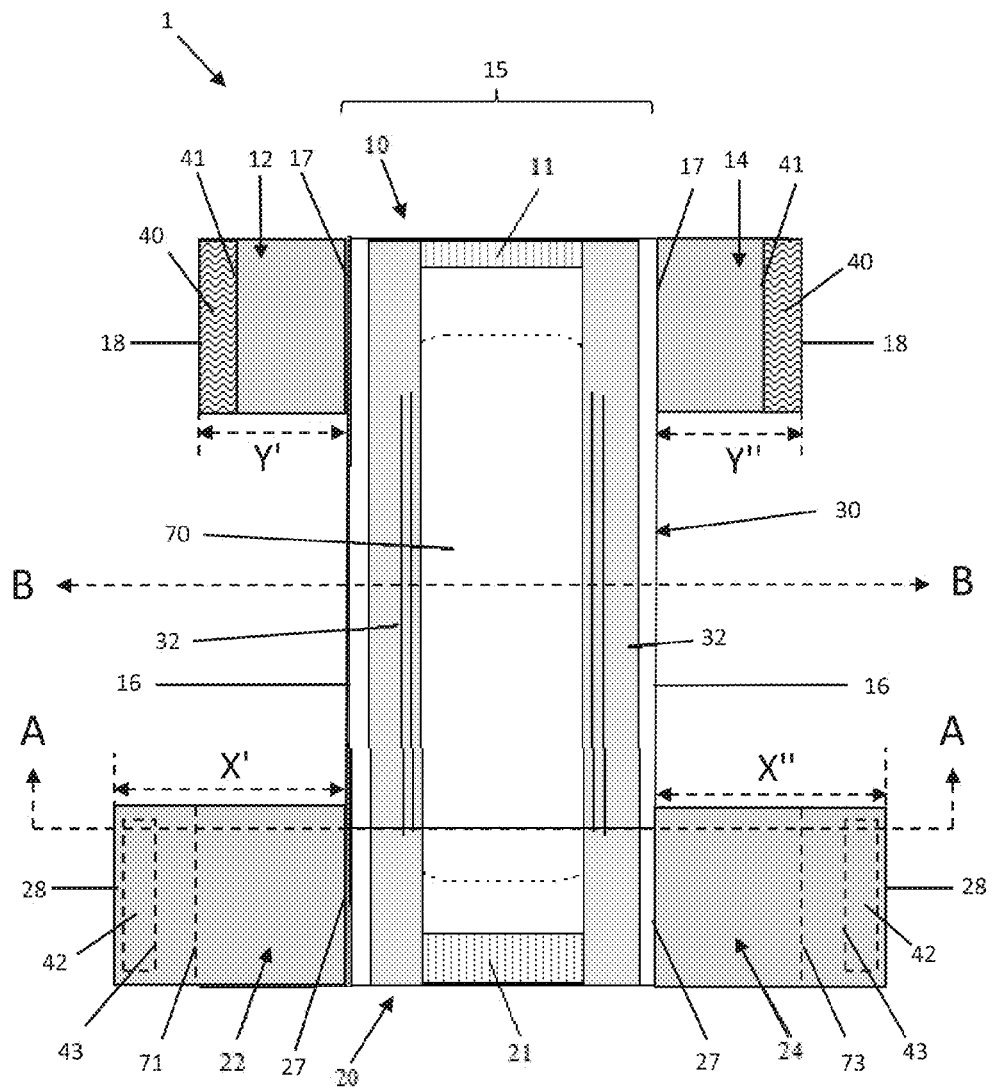
FIG. 1 is a plan view of the inner surface of an absorbent article according to an exemplary embodiment of the invention.

The headings used herein are for organizational purposes only and are not meant to be used to limit the scope of the description or the claims. As used throughout this application, the words "may" and "can" are used in a permissive sense (i.e., meaning having the potential to), rather than the mandatory sense (i.e., meaning must). Similarly, the words "include," "including," and "includes" can mean including but not limited to. To facilitate understanding, like reference numerals have been used, where possible, to designate like elements common to the figures.

DETAILED DESCRIPTION

As used herein, the terms "absorbent article" and "training pant" refer to devices which may be placed against or in proximity to the body of a wearer to absorb and contain various materials discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

Training pants generally include at least a waist opening and two leg openings for accepting the waist and legs of the wearer. Training pants may also include two front side panels that can be coupled to two back side panels forming a seam for securing the training pants to the waist of the wearer. Typical seams are centered on a side portion of the training pant, and can be refastenable, non-refastenable (i.e., "sealed"), or a combination thereof. Refastenable seams can be formed by using fastening components, such as hook and loop fasteners. Hook and loop fasteners may be made up of separate hook and loop elements, or may be integral with the side panels. When overlap refastenable seams are included, training pants may include hook elements on inside or outside surfaces of the side panels. Outward facing hooks are preferable because hook elements can be abrasive and have potential to place the wearer at risk of skin irritation and discomfort if not aligned correctly.

For improved comfort, an absorbent article according to exemplary embodiments of the present invention includes offset overlapped seams with outward-facing hook elements. The outward-facing hook elements may be included on the outside surface of the back side panels, facing away from the user. Including outward facing hook elements may substantially reduce and/or eliminate irritation caused by inward-facing hook elements. In addition to reduction of skin irritation, embodiments of the present invention may also result in absorbent articles that are less stiff, more flexible and more comfortable than prior absorbent articles.

Centered seams present in typical training pants are relatively thick and are somewhat inflexible. To improve the flexibility and comfort of the seam, in exemplary embodiments, an absorbent article includes seams offset toward the front of the absorbent article. By including offset seams, thinner (lower basis weight) front panel material, and a shorter hook length may be used in hook and loop fasteners, so that the seam is substantially thinner and has a lower basis weight than conventional seams. Because the offset seams are thinner, they can also be more flexible than conventional seams.

To offset the seams, back side panels that have greater transverse width than corresponding front side panels may be included, such that the resulting seams are offset toward the front of the absorbent article. The seams may be offset such that the transverse distance of the mating area of the back panel to the chassis of the absorbent article is greater than the transverse distance of the corresponding mating area of the front panel to the chassis. By way of example, the transverse distance from the inner edge of the first fastening element to the outer edge of the chassis may be 2 to 7 times greater than the transverse distance of the inner edge of the second fastening element (mating surface) to the outer edge of the chassis.

Because the offset seams may be thinner than centered seams, the overall basis weight of the seams may be reduced, which can increase the comfort of the training pants. As a result, the seams can be less bulky and can provide increased flexibility. Because seams in accordance with the present invention have a comparatively low basis weight and require less material, they may also provide additional benefits, such as, for example: reduced raw material consumption and cost, reduced environmental pollutants, reduced manufacturing cost, reduced waste, reduced shipping cost, and reduced shelf space and associated storage cost.

In preparation for packaging and/or shipment, the back side panel of the absorbent articles may be folded along an edge, such that the folded edge of the back panel may mate with an unfolded front panel. The seams, which may be refastenable, may be pre-fastened when packaged and/or shipped.

It can also be beneficial to make absorbent articles and training pants more pant-like, such that children and those opposed to wearing training pants may be more inclined and willing to wear them. Accordingly, in exemplary embodiments, absorbent articles may include an overlap seam. Including the overlap seam can result in a smoother, more garment-like absorbent article when compared with absorbent articles including edge to edge ("fin") seams.

To increase flexibility, the front and back side panels may include different materials. For example, the back panel can be substantially elastic and the front (smaller) panel may be substantially non-elastic. As used herein, the terms "elastic" or "elastic materials" are intended to encompass any feasible type of elastic, including an active elastic. The back side panels may be somewhere between 20%-100% elastic. For example, the back side panels may comprise 50% to 80% active elastic. In exemplary embodiments, additional materials may also be included, such as a non-woven and a laminate. The side panels may be discrete panels and at least the back panels may be elastic in the cross direction ("CD"). The side panels may be elastomeric and may have elongation of over 100%. For improved fit, the absorbent article may also include a front waistband and/or a back waistband.

Features and advantages of embodiments the invention will become readily apparent from the following description of an example absorbent article and the accompanying drawings.

Figure 2:
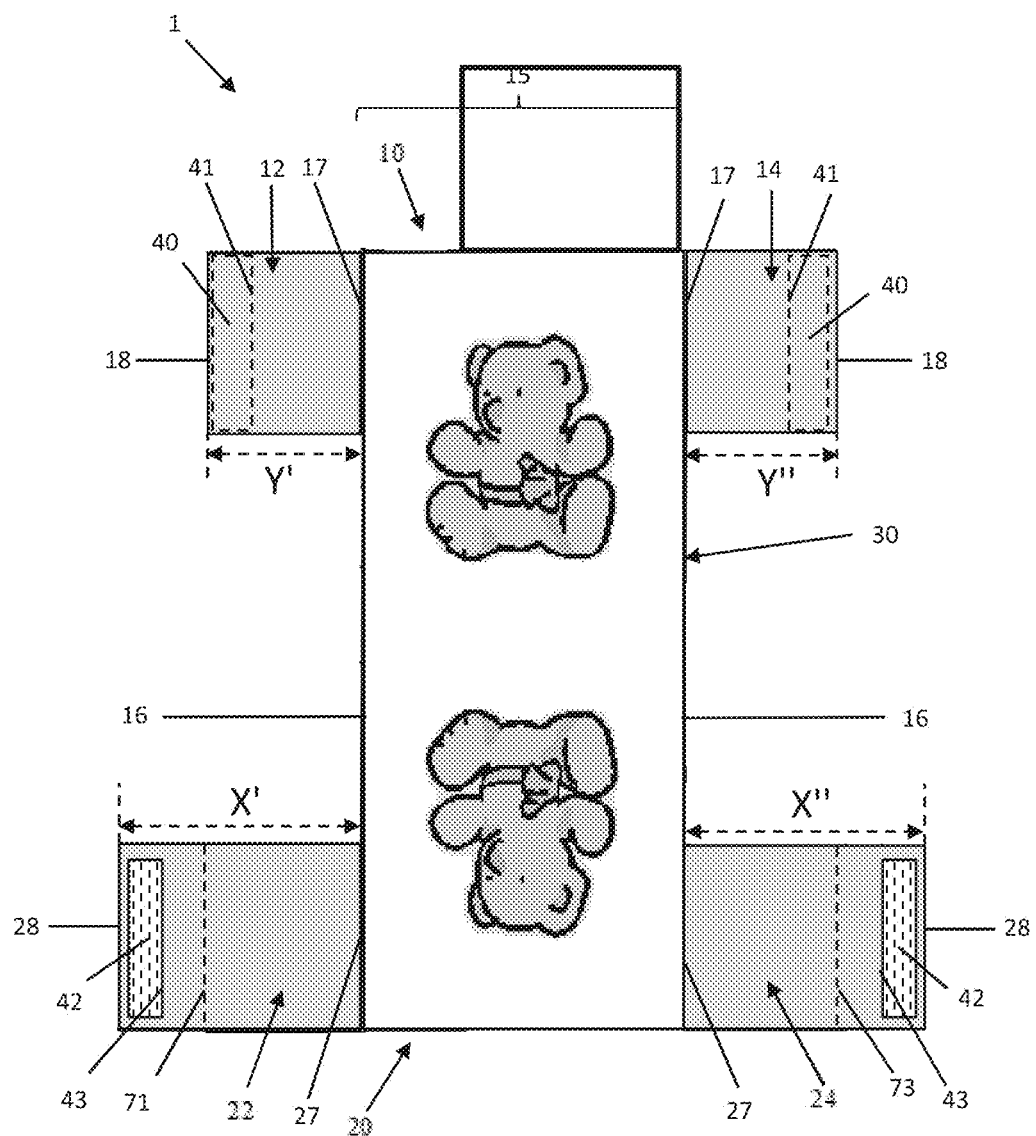
FIG. 2 is a plan view of the outer surface of an absorbent article according to an exemplary embodiment of the invention.

FIGS. 1 and 2 are plan views of an absorbent article, generally designated by reference number 1, according to an exemplary embodiment of the invention. In FIG. 1, the inside surface of the absorbent article 1 is facing upwards, and in the FIG. 2, the outside surface of the absorbent article 1 is facing upwards. In exemplary embodiments, the absorbent article 1 includes a chassis 15 that may include a front waist portion 10, a back waist portion 20, longitudinal edges 16, and a crotch portion 30 longitudinally extending between the front and back waist portions 10, 20.

In exemplary embodiments, the front waist portion 10 may include a first front side panel 12 and second front side panel 14, and the back waist portion 20 may include a first back side panel 22 and a second back side panel 24. The first front side panel 12 and the second front side panel 14 may have an inside surface (shown in FIG. 1), an outside surface (shown in FIG. 2), a proximal edge 17, and a distal edge 18. The first back side panel 22 and the second back side panel 24 may have an inside surface (shown in FIG. 1), an outside surface (shown in FIG. 2), a proximal edge 27 and a distal edge 28. While the front side panels 12, 14 and the back side panels 22, 24 are depicted as being attached in an edge to edge configuration with the chassis 15 in FIGS. 1-2, attachment in an substantially overlapped configuration is contemplated in embodiments of the present invention. Alternatively, the front side panels 12, 14 and the back side panels 22, 24 may be integral with the chassis 15.

Figure 3A:
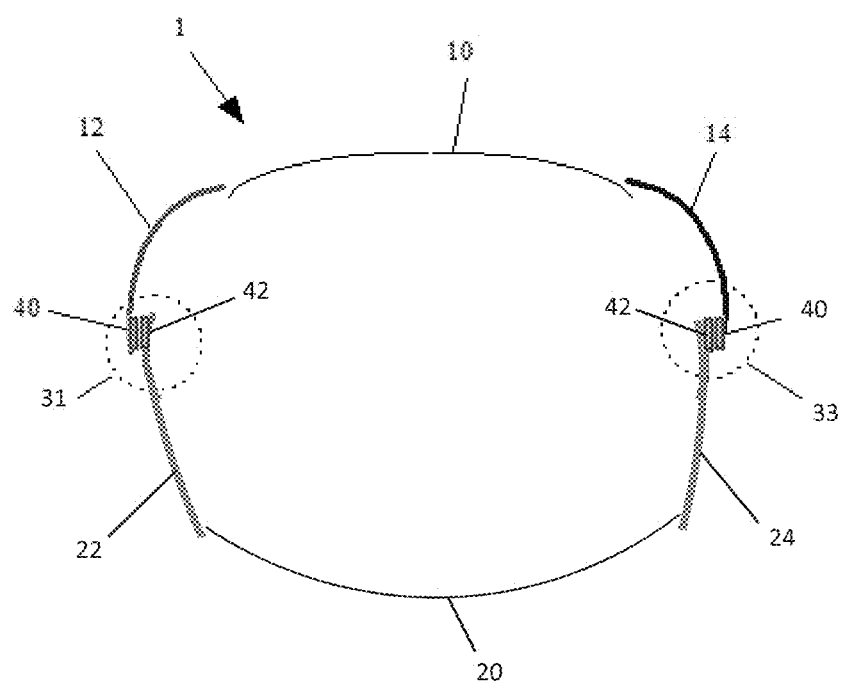
FIG. 3A is a simplified top view of a fastened absorbent article in a worn configuration according to an exemplary embodiment of the invention.

As shown in FIGS. 1 and 2, in exemplary embodiments, the transverse distances X', X" between the proximal edge 27 and distal edges 28 of the first and second back side panels 22, 24 may be greater than the transverse distances Y, Y" between the proximal edge 17 and distal edges 18 of the first and second front side panels 12, 14. While illustrated as substantially equivalent lengths, the transverse distances X', X" may be different lengths, and the transverse distances Y, Y" may be different lengths. As shown in FIG. 3A, when the transverse distances X', X" of the back side panels 22, 24 are greater than the transverse distances Y, Y", the seam created when the front side panels 12, 14 are respectively joined with the back side panels 22, 24 is offset toward the front portion 10. Each of the transverse distances X', X" may be 1.5 to 4 times greater than each of the transverse distances Y, Y".

At least a portion of the first back side panel 22 and the second back side panel 24 may include a material with elastomeric properties. For example, at least a portion of the first back side panel 22 and/or the second back side panel 24 may include an elastic laminate of two layers of nonwoven on either side of an elastic film. The side panels may be formed from elastomeric nonwovens or incorporate elastomeric strands. The elastic material may include up to 10%-90% active elastic. The elastic material may also include elastic properties in the cross-machine direction ("CD") direction, essentially providing a two dimensional stretchability to the material.

The back side panels 22, 24 may be adapted to join with the front side panels 12, 14 with fastening components 40, 42. Although two fastening components 40, 42 are depicted in FIGS. 1-3B, in alternative embodiments only one fastening component may be included. For example, the one fastening component may comprise hook elements adapted to mate with the entire surface of the respective panel. For example, a "loopless" attachment system may be included, as described infra. Also, although hook and loop fasteners are depicted in FIG. 1 and FIG. 2, any type of feasible attachment components can be used.

First fastening components 40 may be disposed on the inside surface of the first front side panel 12 and/or the inside surface of the second front side panel 14. The first fastening components 40 may include, for example, a loop fastener. In alternative embodiments (not shown), the first fastening components 40 may comprise a hook fastener. Second fastening components 42 may be disposed on the outside surface of the first back side panel 22 and/or the outside surface of the second back side panel 24 and may include, for example, a hook fastener. In exemplary embodiments, including a hook fastener facing away from a wearer's body on the outside surface of the first and/or second back side panels 22, 24 may reduce or effectively eliminate irritation when the absorbent article is worn, as compared to absorbent articles in which the hook fastener faces the wearer's body. In addition to the decreased irritation, the comfort of the absorbent article 1 may be increased by including an offset seam.

In an offset seam, the transverse distances between the longitudinal edges 16 of the chassis 15 and inside edges 43 of the second fastening components 42 may be greater than the transverse distances between the longitudinal edges 16 of the chassis 15 and inside edges 41 of the first fastening components 40, creating the offset seam. The transverse distances between the longitudinal edges 16 of the chassis 15 and the inside edges 43 of the second fastening components 42 may be, for example, two to seven times greater than the transverse distances between the longitudinal edges 16 of the chassis 15 and the inside edges 41 of the first fastening components 40. Further, the first and second front side panels 12, 14 and/or the first and second back side panels 22, 24 may be substantially discrete panels.

As shown in FIGS. 1 and 2, in exemplary embodiments, the first back side panel 22 and the second back side panel 24 may include fold lines 71, 73. The fold lines 71, 73 may be adapted to allow distal edges 28 of the back side panels 22, 24 to be folded over toward the inner surface of the absorbent article 1 (See FIG. 3B). The fold lines 71, 73 may be disposed, for example, between the chassis 15 and the fastening components 42. When in a folded condition (See FIG. 3B), the distal edges 28 of the first back side panel 22 and the second back side panel 24 may be folded over about the fold lines 71, 73 such that the first fastening components 40 and the second fastening components 42 can be in position to mate with one another, thereby forming overlap/flat seams when the chassis 15 is folded substantially about an axis B-B passing through the crotch portion 30. An overlap/flat seam is preferred over edge to edge seams because an overlap/flat seam may be smoother and more garment-like than edge to edge seams. In contrast, edge to edge ("fin") seams have exposed bonds that can irritate a wearer. In exemplary embodiments, the seams may be pre-fastened for distribution to consumers, wherein the overlap seam is formed such that the first and second back side panels 22, 24 are folded and mate with the first and second front side panels 12, 14, which may be unfolded.

As shown in FIG. 1, the front waist portion 10 may include a front waist elastic 11 or waistband and the back waist portion 20 may include a back waist elastic 21 or waistband. The front and back waist elastics 11, 21 may provide elasticity to the waist of the absorbent article 1, so that the absorbent article 1 may have a snug fit with the wearer. The front and back elastics 11, 21 may be made up of elongated elastic elements extending transversely across the front and back waist portion 10, 20. In exemplary embodiments, only the front or back waist portions 10, 20 may include elasticized portions. Further, crotch elastics 32 may longitudinally extend through the crotch portion 30 to provide a snug fit in the crotch region of the absorbent article.

As shown in FIG. 3A, which is a simplified top view of a fastened absorbent article 1 in a worn configuration, the first and second fastening components 40, 42 may be used to fasten the first and second front side panels 12, 14 to the first and second back side panels 22, 24, respectively. In this configuration, the absorbent article 1 may be pulled up around the waist of a wearer so as to function as a training pant. The first and second fastening components 40, 42 may form first and second side seams 31, 33 in the absorbent article 1 when in the fastened configuration. The side seams 31, 33 may be refastenable and/or sealed and may be offset from the center of the absorbent article 1.

In exemplary embodiments, the first and second fastening components 40, 42 may form parts of a hook and loop fastening assembly. By way of example, the second fastening components 42 may include Velcro®-like hooks attachable to the first fastening components 40, which may include loop fasteners. Alternatively, the absorbent article 1 may include other types of fastening components 40, 42, such as, for example, adhesives. While two sets of fastening components 40, 42 are depicted in FIGS. 1-3A, the absorbent article 1 may include more or less fastening components. For example, the absorbent article 1 can include only two fastening components adapted to mate with any portion on the entire surface of an opposing side panel in a "loopless" system. One advantage of a "loopless" system may be a thinner seam that is more comfortable for the wearer. Reducing the thickness and basis weight of the seam can generally improve the flexibility and comfort of the absorbent article. As such, in exemplary embodiments, because the side seams 31, 33 are offset closer to the front waist portion 10, shorter hooks may be used when attaching the front side panels 12, 14 to the back side panels 22, 24 such that the thickness and/or basis weight of the seams 31, 33 may be less than the thickness and/or basis weight of a centered seam. By reducing the basis weight and/or thickness of the seams 31, 33, flexibility and comfort of the absorbent article 1 may be increased.

As used herein, the basis weight of the seams 31, 33 may include the combined basis weight of the attached front side and back panels and any fastening components. For example, the basis weight of the seam 31 may include the combined basis weights of the first front side panel 12, the first back side panel 22, and the fastening components 40, 42. In exemplary embodiments, the basis weight of the front panels 12, 14 may be less than the basis weight of the back panels 22, 24. For example, the basis weight of the front panels 12, 14 may be 50% less than the basis weight of the back panels 22, 24. The basis weight of the seams 31, 33 may be between 350-400 grams per square meter ("gsm"). In alternative embodiments, the basis weight of the seam may be between 300-350 gsm. In alternative embodiments, the basis weight of the seams 31, 33 may be less than 300 gsm.

The basis weights of the front side panels 12, 14, the back side panels 22, 24, and the fastening components 40, 42 may be less than conventional absorbent articles. For example, the basis weight of each of the first front side panel 12 and the second front side panel 14 may be approximately 25-75 gsm. The basis weight of the hooks may be, for example, approximately 50-150 gsm. The basis weight of the loops may be, for example, approximately 0-100 gsm, wherein 0 gsm reflects a "loopless" system, as described, infra. The basis weight of an adhesive attaching the hooks to the back side panels 22, 24 may be, for example, approximately 20-80 gsm. The basis weight of each of the first back side panel 22 and the second back side panel 24 may be, for example, approximately 75-160 gsm.

By way of example, the basis weight of the seams 31, 33 may be approximately 325 gsm. The basis weight of the first front side panel 12 and the second front side panel 14 may be, for example, approximately 40 gsm. The basis weight of the hooks may be, for example, approximately 80 gsm. The basis weight of an adhesive attaching the hooks to the back side panels 22, 24 may be, for example, approximately 60 gsm. The basis weight of the first back side panel 22 and the second back side panel 24 may be, for example, approximately 144 gsm.

An advantage of including an offset seams 31, 33 may be a reduced seam thickness, which makes the seam more flexible. As used herein, the thickness of the seam may include the combined thickness of the attached front side and back panels and any fastening components For example, the thickness of the seam 31 may include the combined thickness of the first front side panel 12, the first back side panel 22, and the fastening components 40, 42 in an overlapped configuration. In exemplary embodiments, the thickness of the seams 31, 33 under no amount of compression may be approximately 1 mm-1.5 mm. The thickness of each of the first front side panel 12 and the second front side panel 14 while under no compression may be approximately 0.2 mm-0.5 mm. The thickness of the hooks with an adhesive backing while under no compression may be approximately 0.3 mm-0.5 mm. The thickness of each of the first back side panel 22 and the second back side panel 24 while under no compression may be approximately 0.5 mm-0.8 mm.

By way of example, the thickness of each of the seams 31, 33 while under no compression may be approximately 1.30 mm. The thickness of each of the first front side panel 12 and the second front side panel 14 while under no compression may be approximately 0.28 mm. The thickness of each of the hooks with an adhesive backing while under no compression may be approximately 0.4 mm. The thickness of each of the first back side panel 22 and the second back side panel 24 while under no compression may be approximately 0.62 mm.

In exemplary embodiments, the thickness of the seams 31, 33 under a compressive force of 0.25 pounds per square inch ("psi") or 1.723 kilopascals ("kPa") may be approximately 1 mm-1.5 mm. The thickness of each of the first front side panel 12 and the second front side panel 14 under a compressive force of 0.25 psi (1.723 kPa) may be, for example, approximately 0.2 mm-0.5 mm. The thickness of the hooks with an adhesive backing under a compressive force of 0.25 psi (1.723 kPa) may be, for example, approximately 0.25 mm-0.5 mm. The thickness of each of the first back side panel 22 and the second back side panel 24 under a compressive force of 0.25 psi (1.723 kPa) may be, for example, approximately 0.5 mm-0.8 mm.

By way of example, the thickness of the seams 31, 33 under a compressive force of 0.25 psi (1.723 kPa) may be approximately 1.18 mm. The thickness of each of the first front side panel 12 and the second front side panel 14 under a compressive force of 0.25 psi (1.723 kPa) may be, for example, approximately 0.34 mm. The thickness of the hooks with an adhesive backing under a compressive force of 0.25 psi (1.723 kPa) may be, for example, approximately 0.48 mm. The thickness of each of the first back side panel 22 and the second back side panel 24 under a compressive force of 0.25 psi (1.723 kPa) may be, for example, approximately 0.67 mm.

In exemplary embodiments, the first and second fastening components 40, 42 may form parts of a "loopless" fastening system. That is, the second fastening components 42 may include Velcro®-like hooks that are attachable to an inner nonwoven surface of the first and second front side panels 12, 14, respectively. In this regard, the hooks of the second fastening components 42 may not require special landing zones. Instead, the entire inner surface of the front panel 1 may function as a landing zone for the hooks so as to provide an increased degree of flexibility in the fitting of the absorbent article 1 to a wearer. Such a loopless fastener system is described in U.S. Patent Application Publication No. US 2003/0220626 A1, filed on May 7, 2003, now abandoned, and in U.S. Patent Application Publication No. 2008/0132867, filed Nov. 30, 2006, the contents of which are incorporated herein by reference in their entirety The absorbent article 1 may also be provided in different sizes to accommodate wearers of various sized waists and legs. In exemplary embodiments, the first and second fastening components 40, 42 may have, for example, a vertical length in the range of 50 mm to 130 mm. For increased adjustability, the absorbent article 1 may also be adapted to conform to the legs and waist of the user using waist elastics.

The first and second fastening components 40, 42 may include, for example, a longitudinal length in the range of 50 mm to 130 mm. The first and second fastening components 40, 42 may include, for example, base layers having back surfaces and front surfaces. The base layers may include, for example, a nonwoven material layer or a polymeric material layer. The back surfaces of the first fastening components 40 may be attached to the inner surface of the first front side panel 12 and/or the inner surface of the second front side panel 14 by, for example, adhesive, ultrasonic or thermal sealing.

Further, in exemplary embodiments, the back surfaces of the second fastening components 42 may be attached to the outer surface of the first back side panel 22 and/or the outer surface of the second back side panel 24 by, for example, adhesive, ultrasonic or thermal sealing. Alternatively, the second fastening components 42 may be integral to the outer surface of the first back side panel 22 and/or the outer surface of the second back side panel 24. The front surface(s) of the front first fastening components 40 may include loop fasteners and the front surfaces of the second fastening components 42 may include, for example, hook elements.

Figure 3B:
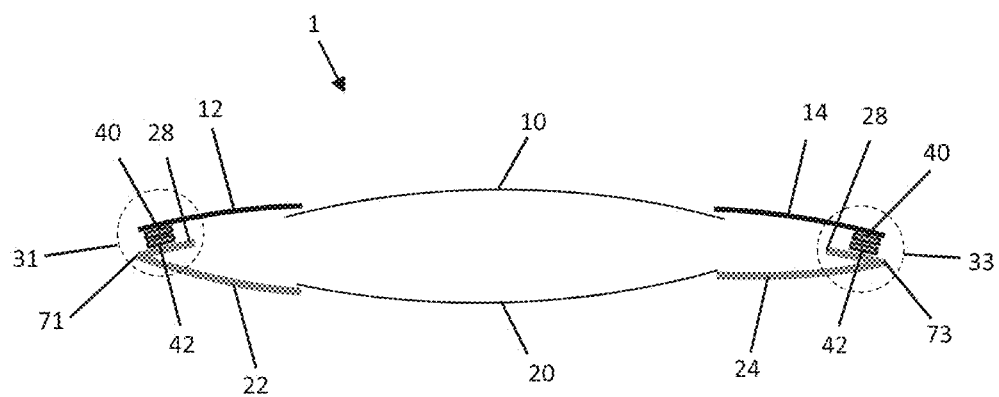
FIG. 3B is a simplified top view of a fastened absorbent article in a folded configuration according to an exemplary embodiment of the invention.

As shown in FIG. 3B, which is a simplified top view of a fastened absorbent article 1 in a folded configuration, the fold lines 71, 73 are adapted to allow the distal edges 28 of the back side panels 22, 24 to be folded over toward the inner surface of the absorbent article 1. When in a folded condition as shown, the distal edges 28 of the back side panels 22, 24 are folded over about the fold lines 71, 73 such that the first fastening components 40 and the second fastening components 42 are in position to mate with one another, thereby forming offset overlapping side seams 31, 33.

Figure 4:
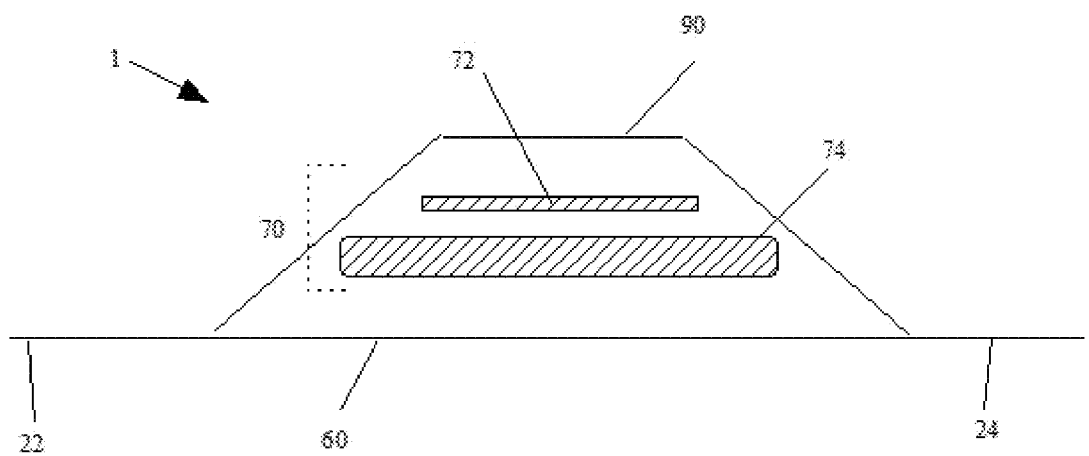
FIG. 4 is a cross-sectional view taken along the line A-A in FIG. 1.

FIG. 4 is a cross-sectional view of the absorbent article 1 taken along the line A-A of FIG. 1. As shown in FIG. 4, the absorbent article is a layered structure including a backsheet 60 and a topsheet 90. In exemplary embodiments, an absorbent assembly 70 may be disposed between the backsheet 60 and topsheet 90. The absorbent assembly 70 may include an acquisition/distribution layer 72 and an absorbent member 74. As shown in FIG. 4, portions of the backsheet 60 may extend beyond the other layers of the absorbent article 1 to form the first and second front side panels 12, 14 and the first and second back side panels 22, 24. However, it should be appreciated that, in exemplary embodiments, the first and second front side panels 12, 14 and first and second back side panels 22, 24 may be formed by extending portions of the topsheet 90, extending portions of both the backsheet 60 and topsheet 90, or by layering other materials with either one or both of the backsheet 60 and topsheet 90. The first and second front side panels 12, 14 and first and second back side panels 22, 24 may be formed separately from the backsheet 60 and topsheet 90. The first and second front side panels 12, 14 and the first and second back side panels 22, 24 may be made breathable, non-breathable, elastic, non-elastic, liquid pervious, liquid non-pervious, or include any other desired characteristic depending on the particular materials and construction used to form the side panels.

The topsheet 90 may be made of any suitable relatively liquid-pervious material currently known in the art or later discovered that permits passage of a liquid therethrough. Examples of suitable top sheet materials may include nonwoven, spun-bonded or carded webs of polypropylene, polyethelene, nylon, polyester and blends of these materials, or perforated, apertured or reticulated films, and the like. Nonwoven materials are exemplary because such materials readily allow the passage of liquids to the underlying acquisition layer 72, and therethrough to absorbent core 74. The top sheet 90 is may be formed of a single ply of nonwoven material that may be made of thermally bonded, spunbonded fibers, spunbond-meltblown-spunbond or fibers that have been hydroentangled, having a basis weight of, for example, 8-30 grams per square meter and having appropriate strength and softness for use as a topsheet in an application which will be in contact with human skin. In exemplary embodiments, the topsheet 90 may be treated with surfactant, which may be rendered hydrophilic to facilitate the passage of moisture through topsheet 90 and into the interior of absorbent assembly 70. Exemplary embodiments of the invention are not intended to be limited to any particular material for top sheet 90 and other top sheet materials will be readily apparent to those skilled in the art.

In exemplary embodiments, acquisition/distribution layer 72 may be a single layer or multiple layers made of synthetic or natural material, or a combination of both, or a single multilayer apertured film. The acquisition/distribution layer 72 may serve to quickly collect and distribute discharged body fluid to absorbent core 74. Because such fluid is typically discharged in gushes, the area of absorbent core 74 proximate to the point of fluid discharge may be overwhelmed by its rate, resulting in a leak. Therefore, the acquisition/distribution layer 72 may facilitate transport of the fluid from the point of discharge across its surface area to contact other parts of absorbent core 74 from which it may be more readily absorbed. In exemplary embodiments, absorbent core 26 may have the construction disclosed in U.S. Pat. Nos. 6,068,620 and 6,646,180 to Chmielewski, both of which are hereby incorporated by reference in their entirety.

Absorbent core 74 may be any absorbent material which may generally be compressible, may be conformable to the shape of the wearer's body and may not impede normal movement by the wearer, and capable of absorbing and retaining liquids such as urine and certain other body exudates. The absorbent core 74 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles, such as, for example, wood pulp fluff. Examples of other suitable absorbent materials include creped cellulose wadding; meltblown polymers; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials, to name a few.

In exemplary embodiments, the configuration and construction of absorbent core 74 may also be varied (e.g., the absorbent core may have varying caliper zones, a hydrophilic gradient, an absorbent gelling material gradient, or lower average density and lower average basis weight acquisition zones; or may include one or more layers or structures, i.e., members, including sheets or webs). In addition, each member need not be formed of a single unitary piece of material, but may be formed of a number of smaller strips or components joined together lengthwise or width-wise, as long as they are in fluid communication with one another. In exemplary embodiments, the total absorbent capacity of absorbent core 74 may be compatible with the design loading and the intended use of the absorbent article 1. Further, the size and absorbent capacity of the absorbent core 74 may be varied to accommodate wearers ranging from infants through adults.

In exemplary embodiments, backsheet 60 may be made of an inner layer of film that is suitably pliable and liquid impervious and an outer layer of a liquid and/or vapor-pervious material. By way of example, typical materials for the backsheet 60 inner layer may include films of polyethylene, polypropylene, polyester, nylon and polyvinyl chloride and blends of these materials, to name a few. In exemplary embodiments, the inner layer may be made of a polyethylene film having a thickness in the range of 0.5 to 2.0 mils. Other backsheet inner layer materials may be readily apparent to those skilled in the art. A backsheet inner layer may be included, that has sufficient liquid imperviousness to prevent leakage of fluids. The required level of liquid imperviousness may vary between different locations on absorbent article 1. Accordingly, the backsheet inner layer may be made vapor pervious or multi layered, having varying degrees of liquid-imperviousness.

The outer layer of the backsheet 60 may be made of a liquid and/or vapor-pervious material which may be selected from the same group of materials from which the top sheet was selected. The inner layer of the backsheet 60 may have a basis weight of, for example, between 5-45 grams per square meter. Unlike topsheet 90, however, the material used for the outer layer of the backsheet 60 may be rendered hydrophobic by omitting the surfactant discussed above with respect to topsheet 90.

In exemplary embodiments, backsheet 60 may have the same or greater longitudinal dimension to that of absorbent assembly 70. Also, the longitudinal dimension of at least the inner layer of the backsheet 60 may be greater than that of the absorbent assembly 70. The inner layer and the outer layer, or only the outer layer, of the backsheet 60 may extend beyond the absorbent assembly 70 to form that first and second front side panels 12, 14 and the first and second back side panels 22, 24.

The absorbent assembly 70 may be self contained, for example, by adhering the perimeter of topsheet 90 to the inner layer of the backsheet 60, such as with ordinary adhesive, or by bonding, with heat or ultrasonically, the components to each other. The acquisition/distribution layer 72 and the absorbent core 74 may be contained within a package formed by the inner layer of the backsheet 60 and the topsheet 90. The absorbent assembly 70 may be adhered to outer layer of the backsheet 60. The topsheet 90 may be adhered directly to the outer layer of the backsheet 60, so that the topsheet 90 may secure the components of the absorbent assembly 70 between the backsheet 60 and the topsheet 90.

While particular embodiments of the invention have been illustrated and described, it would be obvious to those skilled in the art that various other changes and modifications may be made without departing from the spirit and scope of the invention. It is therefore intended to cover in the appended claims all such changes and modifications that are within the scope of this invention.

It will be understood that any of the steps described may be rearranged, separated, and/or combined without deviating from the scope of embodiments of the invention. For ease, steps are, at times, presented sequentially. This is merely for ease and is in no way meant to be a limitation.

Further, it will be understood that any of the elements and/or exemplary embodiments of the invention described may be rearranged, separated, and/or combined without deviating from the scope of the invention. For ease, various elements are described, at times, separately. This is merely for ease and is in no way meant to be a limitation.

While the various steps, elements, and/or exemplary embodiments of the invention have been outlined above, it is evident that many alternatives, modifications and variations will be apparent to those skilled in the art. The various steps, elements, and/or exemplary embodiments of the invention, as set forth above, are intended to be illustrative, not limiting. Various changes may be made without departing from the spirit and scope of the invention. Accordingly, the spirit and scope of the disclosure is to be construed broadly and not limited by the foregoing specification.

No element, act, or instruction used in the description of the present application should be construed as critical or essential to embodiments of the invention unless explicitly described as such. Also, as used herein, the article "a" is intended to include one or more items. Where only one item is intended, the term "one" or similar language is used.

Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items. In addition, as used herein, the term "set" is intended to include any number of items, including zero. Further, as used herein, the term "number" is intended to include any number, including zero.

What is claimed is:

1. An absorbent article comprising:
   a chassis comprising a front waist portion and a back waist portion;
   a pair of front side panels extending outwardly from the front waist portion, the front side panels having an inside surface, an outside surface, a proximal edge, and a distal edge;
   a pair of back side panels extending outwardly from the back waist portion, the back side panels having an inside surface, an outside surface, a proximal edge, and a distal edge, the transverse distance between the proximal edge and the distal edge of each panel of the pair of back side panels being between 1.5 and 4 times greater than the transverse distance between the proximal edge and the distal edge of each panel of the pair of front side panels; and
   a pair of refastenable side seams adapted to attach the front side panels to the back side panels in an overlapped configuration offset toward the front waist portion, wherein each seam of the pair of refastenable side seams has a basis weight of less than 400 grams per square meter, the refastenable side seams comprising first fastening components positioned at the outside surface of each back side panel and second fastening components positioned at the inside surface of each front side panel.

2. The absorbent article of claim 1, wherein each seam of the pair of refastenable side seams has a basis weight of 350 to 400 grams per square meter.

3. The absorbent article of claim 1, wherein a portion of each front side panel at which the front side panel is attached to a corresponding one of the back side panels by a corresponding one of the refastenable side seams has a basis weight of from 25 grams per square meter to 75 grams per square meter.

4. The absorbent article of claim 1, wherein a portion of each back side panel at which the back side panel is attached to a corresponding one of the front side panels by a corresponding one of the refastenable side seams has a basis weight of from 75 grams per square meter to 160 grams per square meter.

5. The absorbent article of claim 1, wherein each first fastening component has a basis weight of from 50 grams per square meter to 150 grams per square meter.

6. The absorbent article of claim 1, wherein the chassis further comprises:
   a liquid pervious topsheet;
   a backsheet, at least a portion of the backsheet being liquid impervious; and
   an absorbent core disposed between the topsheet and the backsheet.

7. The absorbent article of claim 1, wherein the transverse distance between the proximal edge and the distal edge of at least one panel of the pair of back side panels is about double the transverse distance between the proximal edge and the distal edge of at least one panel of the pair of front side panels.

8. The absorbent article of claim 1, wherein the average basis weight of the pair of front side panels is less than the average basis weight of the pair of back side panels.

9. The absorbent article of claim 1, wherein the average basis weight of the front side panels is less than half the average basis weight of the pair of back side panels.

10. The absorbent article of claim 1, wherein at least a portion of each panel of the pair of back side panels is elastic.

11. The absorbent article of claim 1, wherein at least a portion of each panel of the pair of front side panels is non-elastic.

12. The absorbent article of claim 1, wherein at least a portion of each panel of the pair of back side panels comprises a material that is substantially elastic in two dimensions.

13. The absorbent article of claim 1, wherein each back side panel comprises a folded edge and each front side panel comprises a non-folded edge.

14. The absorbent article of claim 1, wherein the first fastening components comprise a hook fastener.

15. The absorbent article of claim 1, wherein the second fastening components comprise a loop fastener.

16. The absorbent article of claim 1, wherein the transverse distance from an inner edge of each of the first fastening elements to an outer edge of the chassis is 2 to 7 times greater than the transverse distance from an inner edge of the second fastening elements to an outer edge of the chassis.

17. An absorbent article comprising:
a chassis comprising a front waist portion and a back waist portion;
a pair of front side panels extending outwardly from the front waist portion, each front side panel having an inside surface, an outside surface, a proximal edge, and a distal edge;
a pair of back side panels extending outwardly from the back waist portion, each back side panel having an inside surface, an outside surface, a proximal edge, and a distal edge, the transverse distance between the proximal edge and the distal of each panel of the pair of back side panels being between 1.5 and 4 times greater than the transverse distance between the proximal edge and the distal edge of each panel of the pair of front side panels; and
a pair of non-refastenable, sealed side seams joining the front side panels to the back side panels, the pair of sealed side seams being adapted to attach the front side panels to the back side panels in an overlapped configuration offset toward the front waist portion.

18. The absorbent article of claim 17, wherein each seam of the pair of sealed side seams has a basis weight of less than 400 grams per square meter.

19. The absorbent article of claim 17, wherein a portion of each front side panel at which the front side panel is attached to a corresponding one of the back side panels by a corresponding one of the sealed side seams has a basis weight of from 25 grams per square meter to 75 grams per square meter.

20. The absorbent article of claim 17, wherein a portion of each back side panel at which the back side panel is attached to a corresponding one of the front side panels by a corresponding one of the sealed side seams has a basis weight of from 75 grams per square meter to 160 grams per square meter.

21. The absorbent article of claim 17, wherein the chassis comprises:
a liquid pervious topsheet;
a backsheet, at least a portion of the backsheet being liquid impervious; and
an absorbent core disposed between the topsheet and the backsheet.

22. The absorbent article of claim 17, wherein the transverse distance between the proximal edge and the distal edge of at least one of the back side panels is about double the transverse distance between the proximal edge and the distal edge of at least one of the front side panels.

23. The absorbent article of claim 17, wherein the average basis weight of the pair of front side panels is less than the average basis weight of the pair of back side panels.

24. The absorbent article of claim 17, wherein the average basis weight of the pair of front side panels is less than half of the average basis weight of the pair of back side panels.

25. The absorbent article of claim 17, wherein at least a portion of at least one panel of the pair of back side panels is elastic.

26. The absorbent article of claim 17, wherein at least a portion of at least one panel of the pair of front side panels is non-elastic.

27. The absorbent article of claim 25, wherein at least a portion of at least one panel of the pair of back side panels comprises a material that is substantially elastic in two dimensions.

28. An absorbent article comprising:
a chassis comprising a front waist portion and a back waist portion;
a pair of front side panels extending outwardly from the front waist portion, the front side panels having an inside surface, an outside surface, a proximal edge, and a distal edge;
a pair of back side panels extending outwardly from the back waist portion, the back side panels having an inside surface, an outside surface, a proximal edge, and a distal edge, the transverse distance between the proximal edge and the distal edge of each panel of the pair of back side panels being between 1.5 and 4 times greater than the transverse distance between the proximal edge and the distal edge of each panel of the pair of front side panels; and
a pair of refastenable side seams adapted to attach the front side panels to the back side panels in an overlapped configuration offset toward the front waist portion, the refastenable side seams comprising one or more first fastening components positioned at the outside surface of each back side panel and one or more second fastening components positioned at the inside surface of each front side panel.

29. The absorbent article of claim 28, wherein each refastenable side seam has a basis weight of from 350 to 400 grams per square meter.

30. The absorbent article of claim 28, wherein a portion of each front side panel attached to a corresponding one of the back side panels by a corresponding one of the refastenable side seams has a basis weight from 25 grams per square meter to 75 grams per square meter.

31. The absorbent article of claim 28, wherein a portion of each back side panel attached to a corresponding one of the front side panels by a corresponding one of the refastenable side seams has a basis weight from 75 grams per square meter to 160 grams per square meter.

32. The absorbent article of claim 28, wherein each of the one or more first fastening components has a basis weight from 50 grams per square meter to 150 grams per square meter.

33. The absorbent article of claim 28, wherein the chassis further comprises:
a liquid pervious topsheet;
a backsheet, at least a portion of the backsheet being liquid impervious; and
an absorbent core disposed between the topsheet and the backsheet.

34. The absorbent article of claim 28, wherein the transverse distance between the proximal edge and the distal edge of at least one panel of the pair of back side panels is at least double the transverse distance between the proximal edge and the distal edge of at least one panel of the pair of front side panels.

35. The absorbent article of claim 28, wherein the average basis weight of the pair of front side panels is less than the average basis weight of the pair of back side panels.

36. The absorbent article of claim 28, wherein the average basis weight of the front side panels is less than half the average basis weight of the pair of back side panels.

37. The absorbent article of claim 28, wherein at least a portion of at least one panel of the pair of back side panels is elastic.

38. The absorbent article of claim 28, wherein at least a portion of at least one panel of the pair of front side panels is non-elastic.

39. The absorbent article of claim 28, wherein at least a portion of at least one panel of the pair of back side panels comprises a material that is substantially elastic in two dimensions.

40. The absorbent article of claim 28, wherein each back side panel comprises a folded edge and each front side panel comprises a non-folded edge.

41. The absorbent article of claim 28, wherein the first fastening components comprise a hook fastener.

42. The absorbent article of claim 28, wherein the second fastening components comprise a loop fastener.

43. The absorbent article of claim 28, wherein a transverse distance from an inner edge of each of the first fastening elements to an outer edge of the chassis is 2 to 7 times greater than a transverse distance from an inner edge of each of the second fastening elements to an outer edge of the chassis.

44. An absorbent article comprising:
a chassis comprising a front waist portion and a back waist portion;
a pair of front side panels extending outwardly from the front waist portion, the front side panels having an inside surface, an outside surface, a proximal edge, and a distal edge;
a pair of back side panels extending outwardly from the back waist portion, the back side panels having an inside surface, an outside surface, a proximal edge, and a distal edge, the entire distance between the distal edges of the back side panels being 1.1 to 2 times greater than the entire distance between the distal edges of the front side panels; and
a pair of refastenable side seams adapted to attach the front side panels to the back side panels in an overlapped configuration offset toward the front waist portion.

45. The absorbent article of claim 44, wherein the refastenable side seams comprise one or more first fastener elements positioned at the inside surface of each front side panel, the one or more first fastener elements adapted to attach to the outside surface of each back side panel.

46. The absorbent article of claim 45, wherein each seam of the pair of refastenable side seams has a basis weight of less than 400 grams per square meter.

* * * * *